United States Patent [19]

DePalma et al.

[11] 4,271,209
[45] Jun. 2, 1981

[54] METHOD AND APPARATUS FOR COATING THE GROOVED BOTTOMS OF SUBSTRATES

[75] Inventors: Vito A. DePalma; Anne E. Meyer, both of Tonawanda; Albert K. Ashby, Lancaster, all of N.Y.

[73] Assignee: Calspan Corporation, Buffalo, N.Y.

[21] Appl. No.: 140,906

[22] Filed: Apr. 16, 1980

[51] Int. Cl.³ .............................................. B05D 5/12
[52] U.S. Cl. ...................................... 427/58; 118/53; 427/96; 427/122; 427/123; 427/240; 427/358
[58] Field of Search .................... 118/53; 427/240, 58, 427/96, 358, 122, 123

[56] References Cited

U.S. PATENT DOCUMENTS

| | | | |
|---|---|---|---|
| 3,364,054 | 1/1968 | Weingarten | 427/240 |
| 3,467,059 | 9/1969 | Korner et al. | 118/53 |
| 3,663,273 | 5/1972 | Porter et al. | 118/53 |
| 3,730,760 | 5/1973 | Machmiller | 427/240 |
| 3,749,052 | 7/1973 | Porter et al. | 118/53 |
| 3,749,058 | 7/1973 | Slabaugh | 118/53 |
| 3,828,727 | 8/1974 | Bauerle | 118/53 |
| 3,840,986 | 10/1974 | Schmidtke | 118/53 |
| 4,052,519 | 10/1977 | Prazak | 427/240 |
| 4,089,989 | 5/1978 | White et al. | 427/240 |

Primary Examiner—Ronald H. Smith
Assistant Examiner—Janyce A. Bell
Attorney, Agent, or Firm—Biebel, French & Nauman

[57] ABSTRACT

Uniform and repeatable formation of a resistance element on a substrate is achieved by spinning the coated objects which are still in a wet state while rotating them about an orthogonal axis to subject the wet indicator formulation to centrifugal forces which forces the indicator formulation into contact with the substrate.

18 Claims, 7 Drawing Figures

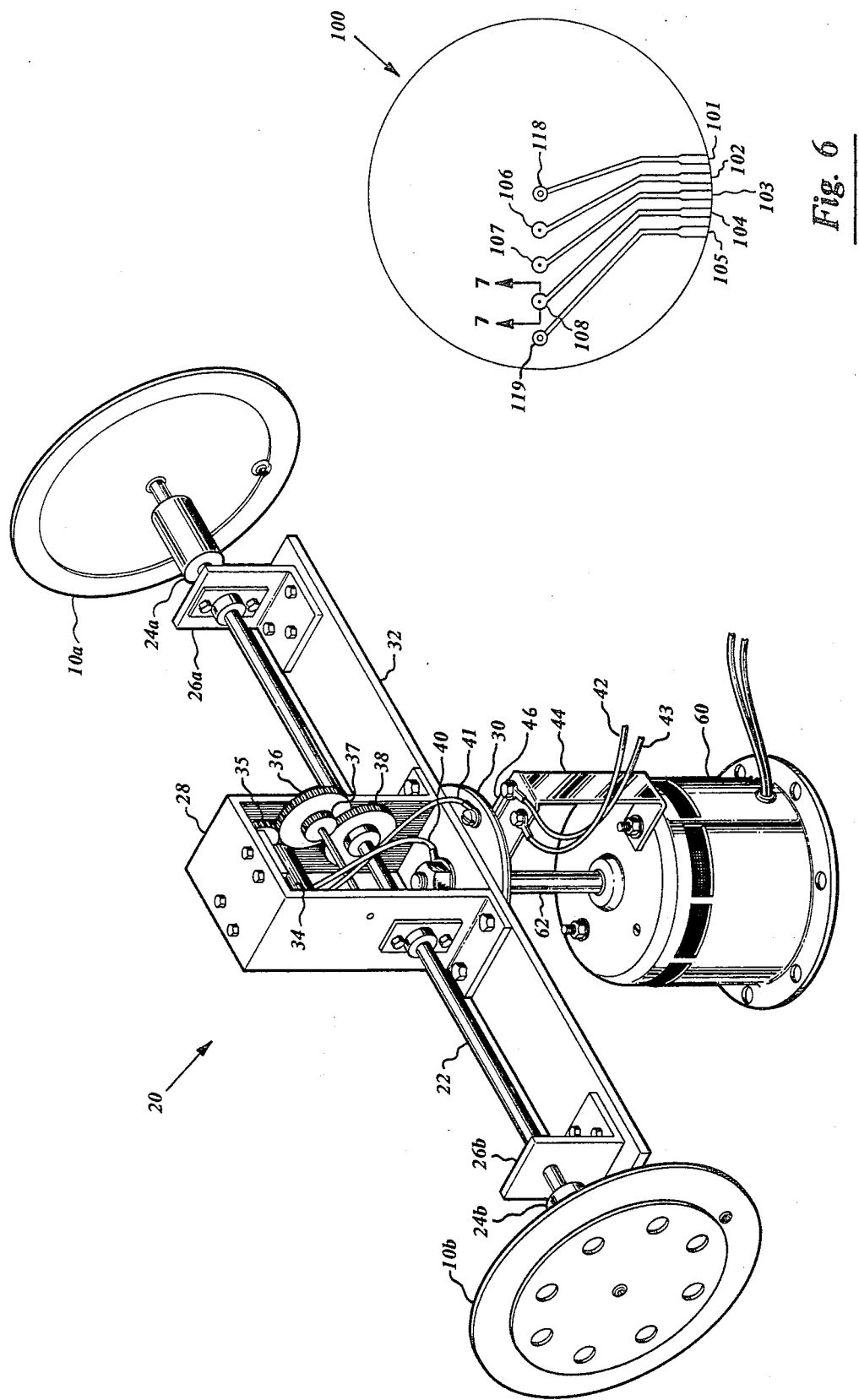

METHOD AND APPARATUS FOR COATING THE GROOVED BOTTOMS OF SUBSTRATES

BACKGROUND OF THE INVENTION

The invention herein described was made in the course of or under a contract with the U.S. Army.

In prior U.S. Pat. No. 4,092,119 various types of indicators for detecting the presence of hazardous chemicals are disclosed, which employ an indicator paint that is responsive to the presence of such chemicals when in contact therewith. The detection is either by a color change, an electrical resistance change or combinations of both. Unfortunately, the indicator paint is also responsive to scuff and abrasion which can cause false indications of the presence of a hazardous chemical. This problem is overcome according to said prior patent by providing a topographically varying surface or substrate the peaks of which extend above the indicator paint to thereby provide protection from scuff and abrasion.

In the case of those indicators having resistance change, an electrically conductive powder is added to the indicator paint and the paint is applied to the substrate in an undulating pattern as by silk-screening. Alternatively, the substrate is dipped into or coated with the indicator paint and cut into circuit elements. When the indicator paint is contacted by a hazardous chemical to which it is responsive, a chemical reaction causes the indicator paint to swell thereby separating the conductive powder particles which causes an increase in the electrical resistance of the indicator. If the indicator is incorporated into an electrical circuit, this increase in resistance can be detected to actuate an alarm or the like. In such circuits the indicator and its substrate are expendable, whereas the other circuit elements are used repeatedly. It is, therefore, extremely important that the resistivity of the conductive paint remain essentially uniform and stable from batch to batch. In this manner unnecessary and time-consuming circuit adjustments can be avoided whenever a new indicator is replaced.

Moreover, since the nature of the reaction between the chemical to be detected (usually in the form of an aerosol or droplet) and the conductive indicator paint is such that the resistance of the paint is increased, it is important that the geometry and size relationship between the two be such that only increases in resistance due to the chemical are detected whereby false alarms as a result of extraneous materials, such as rain, can be minimized.

In situations where the chemical droplets to be detected are very small, the indicator paint must also be extremely small in terms of cross section so that enough chemical will be present to produce the required resistance change. This requirement creates the manufacturing problem of potential physical breaks in the circuitry of the indicator which would cause false alarms due to the increase in resistance caused by such breaks. Thus, the manufacture of the substrate and the manner in which the indicator paint is applied thereto are extremely critical in achieving a successfully operating indicator.

SUMMARY OF THE INVENTION

The foregoing problems are overcome according to the teachings of the present invention which provides a method and apparatus for coating the bottom of grooved substrates in such a manner that the coating material is uniformly distributed therein whereby the resistivity thereof remains essentially stable.

According to one aspect the present invention provides a method of coating a grooved substrate which includes applying a fluent coating material or paint to the substrate, spinning the substrate about a horizontal axis while rotating the same about a vertical axis at a much higher rate whereby the coating material is centrifugally forced into intimate contact with the groove or grooves of the substrate and caused to be uniformly spread therealong.

According to a second aspect, the present invention provides an apparatus for providing simultaneous rotation of the substrate about a vertical axis and spinning thereof about a horizontal axis.

More specifically the present invention provides a method and apparatus for achieving an essentially uniform distribution of a conductive powder-laden indicator paint in the spiral groove within the substrate to thereby repeatably produce indicators having a predetermined initial resistance. The coating process takes place in a number of steps and utilizes centrifugal force to achieve the uniform distribution of conductive powder-laden indicator paint. Because of the tendency for metal powder to rapidly settle out of suspension, the sequence of steps has been developed so as to overcome this tendency. In one step of the coating process, the freshly painted substrates are mounted for rotation about two orthogonal axes. Rotation about one of such axes forces the wet indicator paint into the grooves of the substrates due to centrifugal force, whereas rotation about the other of such axes causes the indicator paint to flow along the bottom of the grooves to uniformly fill the same to the desired depth. This results in such a rapid and simultaneous filling of the groove or grooves that the metal powder does not have time to settle out of suspension.

It is, accordingly, an object of this invention to provide a method and apparatus for producing an indicator having a uniform thickness, compaction and metal distribution of the metal powder-laden indicator formulation on the substrate, and for repeatably producing an indicator having a predetermined initial resistance. This object, and others as will become apparent hereinafter, is accomplished by the present invention.

BRIEF DESCRIPTION OF THE DRAWINGS

For a fuller understanding of the present invention, reference should now be made to the following detailed description thereof taken in conjunction with the accompanying drawings wherein:

FIG. 5 is a pictorial view of the spin/centrifuge apparatus;

FIG. 6 is a bottom view of a modified detector;

DESCRIPTION OF THE PREFERRED EMBODIMENTS

Figure 1:
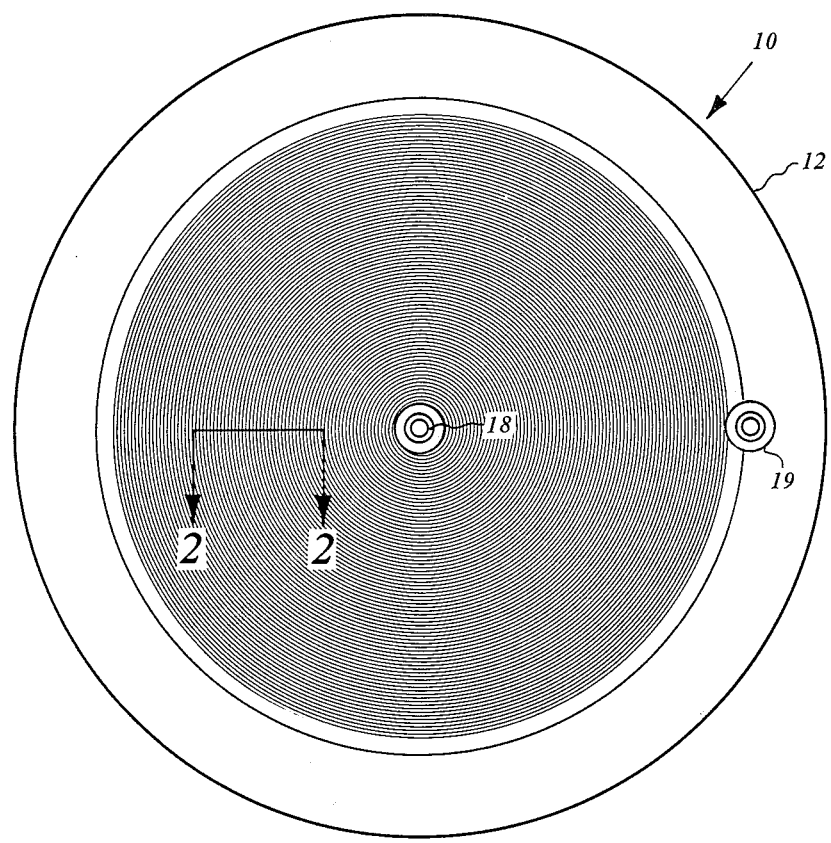
FIG. 1 is a top view of a detector made according to the method of the present invention.
Figure 2:
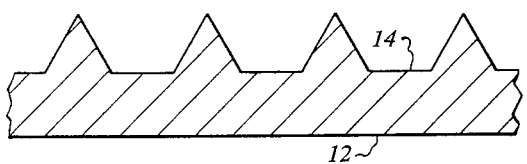
FIG. 2 is a partial sectional view taken along line 2—2 of FIG. 1 and illustrating an unpainted substrate.
Figure 4:
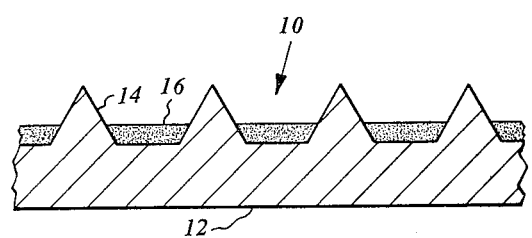
FIG. 4 is a partial sectional view similar to FIG. 3 of a painted substrate after the spin/centrifuge treatment.

In FIG. 1, the numeral 10 generally designates an indicator made according to the present invention. The indicator 10 includes an injection molded nylon substrate 12 the face of which has a wide bottom spiral groove 14 formed therein, as is best shown in FIG. 2. The substantially planar bottom of groove 14 contains the indicator formulation or paint 16 containing an electrically conductive powder, preferably silver or graphite, as is best shown in FIG. 4. Metal eyelets 18 and 19, see FIG. 1, are located at the center and periphery, respectively, of the groove 14 and serve to provide electrical connections to a detector circuit (not illustrated).

Figure 3:
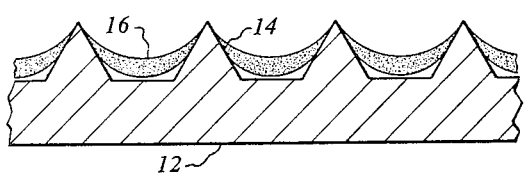
FIG. 3 is a partial sectional view similar to FIG. 2 of a substrate after applying the indicator paint coating.

A sectional view of the unpainted substrate 12 is illustrated in FIG. 2. When the indicator formulation 16 is initially applied to the substrate 12, it tends to have a meniscus-like cross section with respect to the sides of groove 14, as is best shown in FIG. 3. The spin/centrifuging step of the present invention causes the flowing of the metal powder laden-indicator formulation 16 into the bottom of the groove 14 as shown in FIG. 4. This has the beneficial effect of keeping the indicator formulation 16 below the scuff and abrasion level as well as to reduce the possibility of an electrical short circuit or bypass being established between adjacent grooves 14. Chemical agents to be detected tend to flow to the bottom of the groove 14 due to the steep sides thereof and upon contacting the indicator formulation or paint 16 tend to wick into and along the groove by capillary action thereby maximizing the opportunity for interaction between the paint and the chemical agent.

The nylon substrate 12 may be formed by injection molding and has a wide bottom spiral groove 14 formed thereon. Fiducial marks are formed on the substrate 12 and serve to locate the eyelets 18 and 19 which are drilled out with a countersink. After washing in detergent, rinsing, and drying, the substrate 12 is ready to be painted. A typical resin blend and solvent blend for an indicator paint formulation for detecting the presence of organophosphorous chemicals such as malathion and parathion are as follows:

| Component | Source | Type of Material | % Parts by Weight |
| --- | --- | --- | --- |
| RESIN BLEND | | | |
| Aroplaz 1700-A9-60 | Ashland Chemical Co. | Silicone-modified, Oil-free, polyester resin fully saturated | 39.8 |
| Santicizer 334F | Monsanto Company | Phosphate Plasticizer | 8.0 |
| Cellosolve Acetate | Union Carbide Corp. | Solvent | 20.9 |
| Aromatic 150 | Exxon Company | Solvent | 20.9 |
| Butyl Alcohol | Union Carbide Corp. | Solvent | 5.2 |
| Butyl Cellosolve | Union Carbide Corp. | Solvent | 5.2 |
| | | | 100.00 |
| SOLVENT BLEND | | | |
| Cellosolve Acetate | Union Carbide Corp. | Solvent | 40.0 |
| Aromatic 150 | Exxon Company | Solvent | 40.0 |
| Butyl Alcohol | Union Carbide Corp. | Solvent | 10.0 |
| Butyl Cellosolve | Union Carbide Corp. | Solvent | 10.0 |
| | | | 100.00 |

To 6.54 ml of the resin blend is added 13.46 gm of silver powder (Alcan MD-750 silver flake) which has been dispersed by ultrasound treatment in 30 ml of the solvent blend. The mixture is constantly agitated to keep the silver powder in suspension.

The substrate 12 is mounted on a vertical shaft for slow rotation, about 10 rpm. For a 13.9 cm diameter disc, 2 ml of the agitated metal powder-laden indicator paint mixture is drawn into a disposable syringe. The paint is applied sparingly to the slowly rotating substrate starting at the outer edge and moving directly to the center. This technique produces a spiral of paint on the substrate. The remainder of the paint in the syringe is applied by direct outward and inward passes over the substrate. Each succeeding inward pass of the syringe terminates further from the center in order to achieve a more uniform paint distribution. After all of the paint is delivered onto the substrate, the rotation is stopped and a sash brush is applied to the paint, using radially outward strokes only. The indicator paint distribution on the indicators 10 at this stage is illustrated in FIG. 3.

Immediately after painting, pairs of indicators 10 are mounted in the spin/centrifuge apparatus 20 of FIG 5. The indicators 10 are mounted at the ends of horizontally oriented shaft 22 which may turn at about 290 rpm. The shaft 22 is also rotated about the axis of vertical shaft 62 at about 1000 rpm. The rotation of the indicators 10 about the vertical axis of shaft 62 forces the indicator formulation 16 into the bottom of grooves 14, as shown in FIG. 4.

If the only axis of rotation was about shaft 62, centrifugal forces on the wet indicator formulation, while being sufficient to force the same into the groove 14, would also cause undesirable streaking or banding of the formulation or paint in a substantially horizontal plane passing through the center of the indicator 10. This is due to the fact that the centrifugal force has resolvable components acting on the paint in all areas of the indicator 10, except at the center thereof. These component forces would cause the paint to be preferentially distributed in such horizontal plane, thereby resulting in nonuniform bands or streaks of paint which would be of unpredictable and nonrepeatable resistance. This problem is overcome by the simultaneous spinning of the indicators about shaft 22 and rotation about the axis of shaft 62 which causes the indicator formulation to be forced both into and along the spiral groove of the indicator by centrifugal force. The result is a uniform distribution of paint and a complete electrical path through the indicator formulation in the spiral groove. After about 5 minutes, the indicators 10 are removed from the spin/centrifuge apparatus 20 and dried.

After drying for at least 15-20 hours at ambient conditions, the indicators 10 are rotated slowly and the peaks of the groove are scraped with a flat metal blade such as a spatula. The scraping removes any indicator formulation from the top of the ridge defining groove 14, thereby essentially eliminating the possibility of cross-circuiting. The indicator formulation at the bottom of groove 14 is not disturbed by the scraping process since the peaks of the groove provide protection against scuff and abrasion. The result is a spiral resistance element formed along the bottom of groove 14.

Metal eyelets 18 and 19, are then secured to the substrate 12. To insure a good electrical connection, a fast drying silver conducting paint is daubed onto the eyelets 18 and 19 as well as the adjacent substrate. Upon drying, the indicator 10 will then be ready for use, when connected to an electrical circuit via eyelets 18 and 19. The indicator formulation 16 in the groove 14 functions as a uniform and constant resistance element of 50,000 ohms, for example. If the indicator formulation 16 in the groove 14 is contacted by a hazardous chemical to which it is responsive, the indicator formulation 16 expands thereby separating the silver particles and increasing the resistance of indicator 10. The electrical circuit can respond to the increased resistance by activating an alarm or the like.

The spin/centrifuge apparatus 20 will now be described in detail. Referring to FIG. 5, two indicators 10a and 10b supported by, and mounted for rotation in a horizontal plane with horizontal shaft 22 via quick-connect couplings 24a and b, respectively. Shaft 22 is supported in bearing relationship by vertical supports 26a and b, motor mount 28 and slip ring disc 30 are secured to base 32. Base 32 is secured to and mounted for rotation about a vertical axis with shaft 62 of motor 60. Motor 34 is mounted in motor mount 28 and drives shaft 22 through a gear train made up of gears 35-38. Two conventional annular slip rings (not illustrated) are located on the bottom of slip ring disc 30 and are electrically connected to motor 34 via leads 40 and 41. Leads 42 and 43 connect a power source (not illustrated) to electrical contacts on non-conducting support 44 to provide electrical communication with the slip rings on disc 30 and thereby motor 34. Only electrical contact 46 is illustrated, and it provides an electrical connection with a slip ring (not illustrated) to thereby complete a connection between leads 43 and 41 to connect the source of power to motor 34. Similarly, lead 42 is connected to lead via an electrical contact and slip ring (not illustrated) to thereby provide a second electrical connection between the source of power and motor 34. The rotational speeds of the motor 34 and its associated gear train 35-38 and motor 60 are such that shaft 62 rotates at a higher rate than shaft 22. For example, shaft 60 may rotate at 1000 rpm whereas shaft 22 may rotate at 290 rpm.

In operation, when motors 34 and 60 are actuated the indicators 10a and 10b are caused to rotate about the axis of shaft 62 and to simultaneously spin about the axis of shaft 22. Rotation of the indicators about a vertical axis cause centrifugal forces which force the coating material into contact with the grooved substrate thereof, whereas spin about the axis of shaft 22 causes the coating to be uniformly spread along the grooved spiral path thereof.

Figure 7:
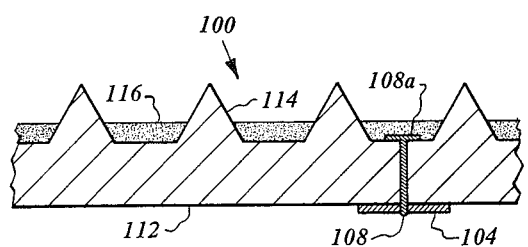
FIG. 7 is a partial sectional view taken along line 7—7 of FIG. 6.

FIG. 6 illustrates a modified indicator 100 having metal eyelets 118 and 119 as in the case of detector 10 of FIGS. 1-5. Additionally, the indicator 100 is provided with printed circuit elements 101, 102, 103, 104 and 105 which are in electrical contact with the metal laden indicator formulation 116 via eyelet 118, metal pins 106, 107 and 108 and eyelet 119 respectively. As shown in FIG. 7, the head 108a of pin 108 is located at the bottom of groove 114 of substrate 112 and is overlain by indicator formulation 116. Because of groove dimensions, to increase the area of contact by the heads of pins 102, 103 and 104, etc. the hole through which the pins are placed may take several coils of the groove 114. The advantage of the indicator 100 over that of indicator 10 is that the detector 100 can be divided into several responsive sections by altering the electrical connections. For example, the various annular areas as between eyelet 118 and pins 106, 107 or 108 may be one area, as may the annular area between pins 106 and 107. Thus, several responsive areas may be defined so as to detect chemical contact at more than one area to give a more quantitative indication of hazardous chemical contact.

Although preferred embodiments of the present invention have been illustrated and described, other changes will occur to those skilled in the art. For example, the number of indicators being spin/centrifuged may be increased and the speeds of spin and rotation may be changed. The spin and rotation speeds may be individually variable and the indicator formulation and conductive particles can be changed as is necessary or desired. It is therefore intended that the scope of the present invention is to be limited only by the scope of the appended claims.

We claim:

1. A method of coating a substrate having at least one groove in a face thereof, including the steps of:
    (1) applying a fluent coating material to said substrate,
    (2) spinning the substrate about an axis perpendicular to the face thereof at a first rate,
    (3) simultaneously rotating said substrate about an axis perpendicular to said first mentioned axis at a second rate that is much greater than said first rate, and
    (4) scraping excess coating material from the face of the substrate.
2. The method according to claim 1, further including the step of
    (5) washing and drying said substrate prior to applying said fluent coating material thereto.
3. The method according to claim 2, wherein;
    (6) said groove comprises a continuous spiral groove in the face of said substrate.
4. The method according to claim 3, wherein;
    (7) said coating material comprises a chemically responsive indicator containing electrically conductive particles.
5. The method according to claim 4, wherein;
    (8) said fluent coating material is initially applied to said substrate as the face thereof is rotated at a slow rate in a horizontal plane.
6. The method according to claim 5, wherein;
    (9) said step of scraping occurs as the face of said substrate is rotated at a slow rate in a horizontal plane.
7. The method according to claim 1, wherein;
    (5) said groove comprises a continuous spiral groove in the face of said substrate.
8. The method according to claim 1, wherein;
    (5) said coating material comprises a chemically responsive indicator containing electrically conductive particles.
9. The method according to claim 1, wherein;

(5) said fluent coating material is initially applied to said substrate as the face thereof is rotated at a slow rate in a horizontal plane.

10. The method according to claim 1, wherein;
(5) said step of scraping occurs as the face of said substrate is rotated at a slow rate in a horizontal plane.

11. A method for forming a chemically responsive electrical resistance element in the spiral groove of a substrate including the steps of:
washing and drying a substrate having a spiral groove therein;
slowly spinning the substrate in a horizontal plane;
applying a chemically responsive indicator coating containing electrically conductive particles to the spinning substrate;
spinning the substrate about a horizontal axis at a first rate while rotating the substrate about a vertical axis at a second rate which is much faster than said first rate, whereby the indicator coating is forced into the spiral groove due to centrifugal force and flows along the groove to achieve a continuous and uniform coating of the bottom of the groove;
drying the indicator formulation; and
scraping the substrate while the substrate is slowly spinning to eliminate electrical connections in the indicator formulation between adjacent coils of the spiral groove whereby the indicator formulation defines an electrical flow path in a spiral pattern defined by the spiral groove and which will change its electrical resistance upon contacting a chemical to which the indicator formulation is responsive.

12. The method of claim 11 wherein said chemically responsive indicator is applied from a syringe while moving the syringe back and forth radially over the slowly spinning substrate.

13. The method of claim 11 further including the step of placing at least two means for establishing electrical contact with said indicator coating in said groove.

14. A spin/centrifuge apparatus for use in a coating process and including:
at least one pair of arms mounted for rotation about a vertical axis;
shaft means supported by said arms for rotation therewith about said vertical axis;
means for independently spinning said shaft means about a horizontal axis;
mounting means at the ends of each of said shaft means for securing the objects to be coated whereby said objects are subject to centrifugal forces due to rotation about said vertical axis which forces a coating material into contact with said objects and whereby said objects are simultaneously subject to spin forces due to said horizontal axis spin to uniformly spread the coating material.

15. A spin/centrifuge apparatus for use in a coating process comprising;
(a) a longitudinally extending base,
(b) means for rotating the base about a vertical axis,
(c) a longitudinally extending shaft substantially coextensive with said base,
(d) means on said base for supporting said shaft for relative rotation about the longitudinal axis thereof,
(e) means for independently spinning said shaft about a horizontal axis, and
(f) mounting means at at least one end of said shaft for securing thereto at least one object to be coated, whereby rotation of said base about said horizontal axis centrifugally forces a coating material in intimate contact with the object to be coated and spinning of said shaft about said horizontal axis causes the coating material to be uniformly spread along the surface of the object to be coated.

16. The apparatus according to claim 15, wherein;
(g) said means for rotating said base comprises a first motor, and
(h) said means for spinning said shaft comprises a second motor.

17. The apparatus according to claim 15, wherein;
(i) said means on said base comprises a member depending perpendicularly from at least one end thereof having an opening through which said shaft protrudes.

18. The apparatus according to claim 15, wherein;
said means on said base comprises a member depending prependicularly from at least one end thereof having an opening through which said shaft protrudes.

* * * * *